United States Patent [19]

Poveromo

[11] Patent Number: 5,286,191

[45] Date of Patent: * Feb. 15, 1994

[54] ONE-PIECE CAST RESIN DENTAL DOWEL WITH VISIBLE HORIZONTAL INDEX

[76] Inventor: Melvin D. Poveromo, 1160 Kane Concourse, Bay Harbor Islands, Miami Beach, Fla. 33154

[*] Notice: The portion of the term of this patent subsequent to Jun. 29, 2010 has been disclaimed.

[21] Appl. No.: 990,522

[22] Filed: Dec. 15, 1992

Related U.S. Application Data

[63] Continuation-in-part of Ser. No. 809,336, Dec. 18, 1991, Pat. No. 5,222,891.

[51] Int. Cl.⁵ ............................................. A61C 19/00
[52] U.S. Cl. ...................................................... 433/74
[58] Field of Search ........................................... 433/74

[56] References Cited

U.S. PATENT DOCUMENTS

| | | | |
|---|---|---|---|
| 2,851,728 | 9/1958 | Spalten et al. | 433/74 |
| 3,413,725 | 12/1968 | Stern et al. | 433/74 |
| 3,454,256 | 7/1969 | Stern et al. | 433/74 |
| 3,470,614 | 10/1969 | Kelly | 433/74 |
| 3,521,354 | 7/1970 | Stern et al. | 433/74 |
| 3,896,548 | 7/1979 | Zahn | 433/74 |
| 4,056,585 | 11/1977 | Waltke | 433/74 |
| 4,139,943 | 2/1979 | Dragan | 433/74 |
| 4,363,625 | 12/1982 | der Avanessian | 433/74 |
| 4,371,340 | 2/1983 | Imaizumi | 433/74 |
| 4,457,709 | 7/1984 | Moore | 433/74 |
| 4,721,464 | 1/1988 | Roden et al. | 433/74 |
| 4,840,565 | 6/1989 | Poveromo | 433/74 |
| 4,997,370 | 3/1991 | Mayclin | 433/74 |

Primary Examiner—John J. Wilson
Attorney, Agent, or Firm—Sughrue, Mion, Zinn, Macpeak & Seas

[57] ABSTRACT

A one-piece molded dental dowel-pin adapted to be fixed to a tooth die and having an integral elongated locking-and-indexing arm which, after final trimming of a dental model, has an outer tip which is visible to a human observer when the tooth die is inserted in the trimmed, final dental model.

10 Claims, 6 Drawing Sheets

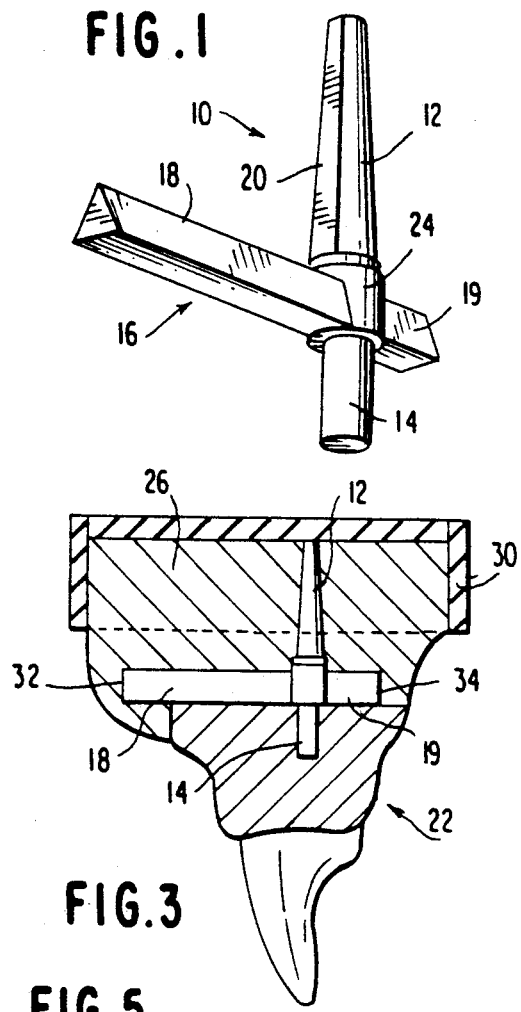
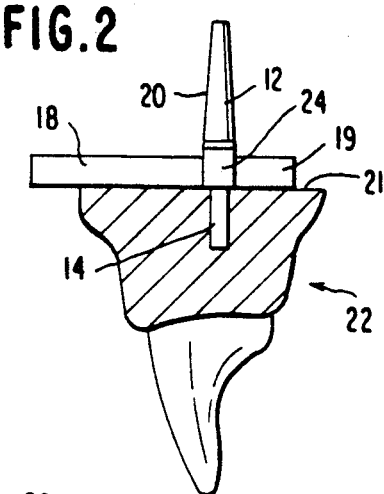
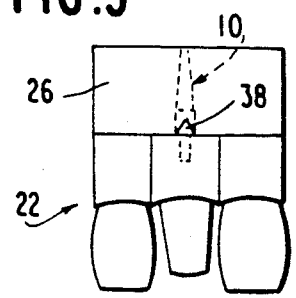
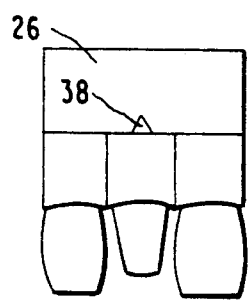
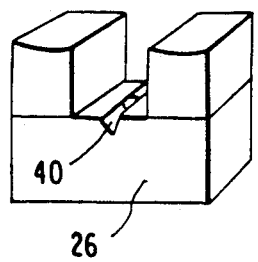
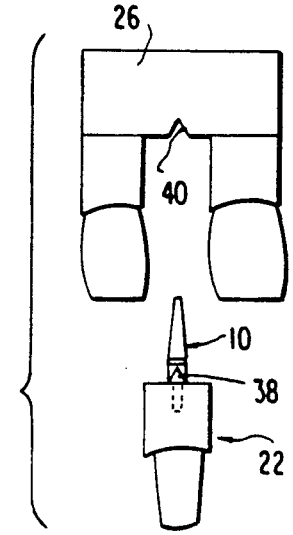

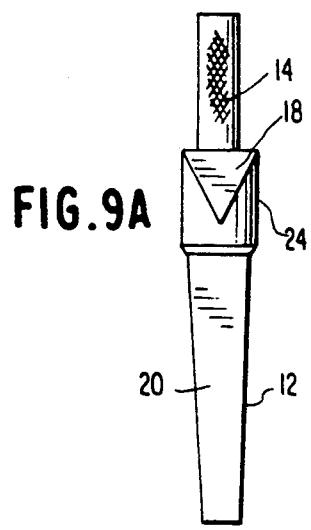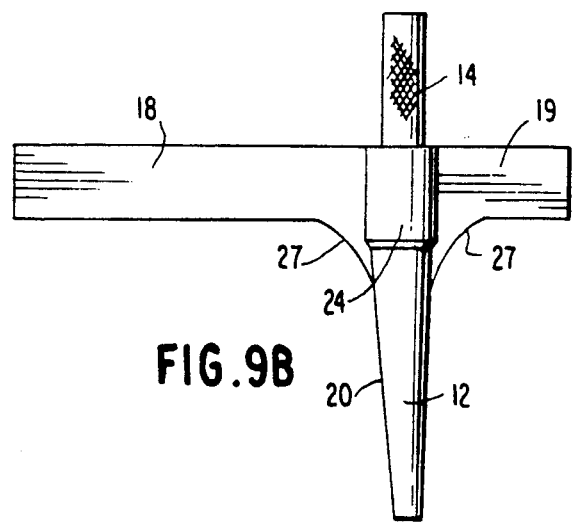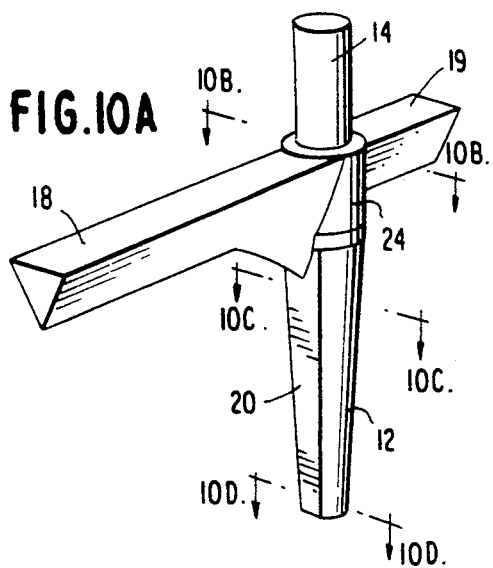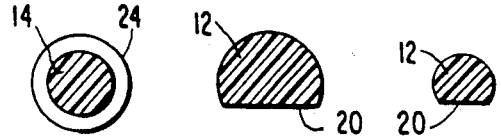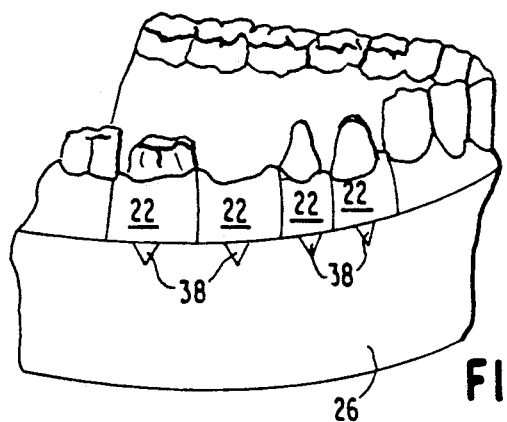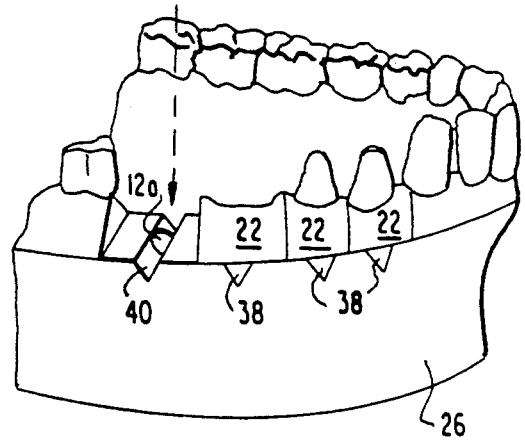

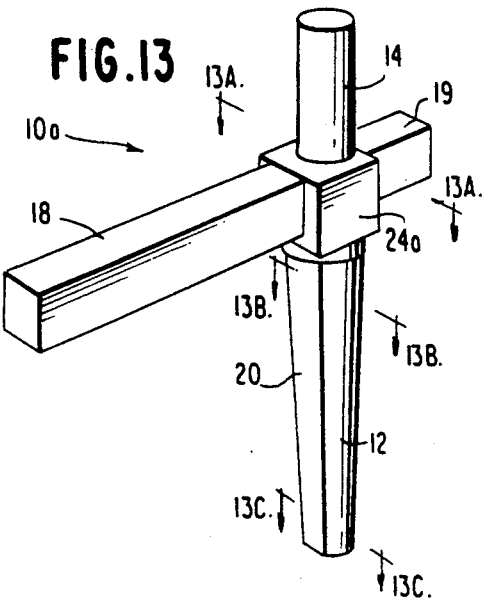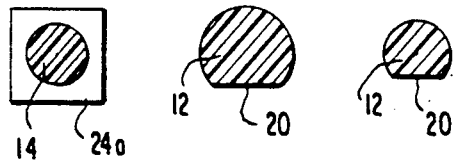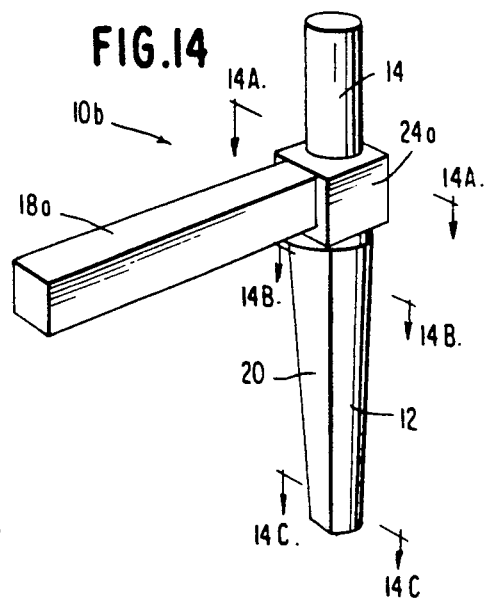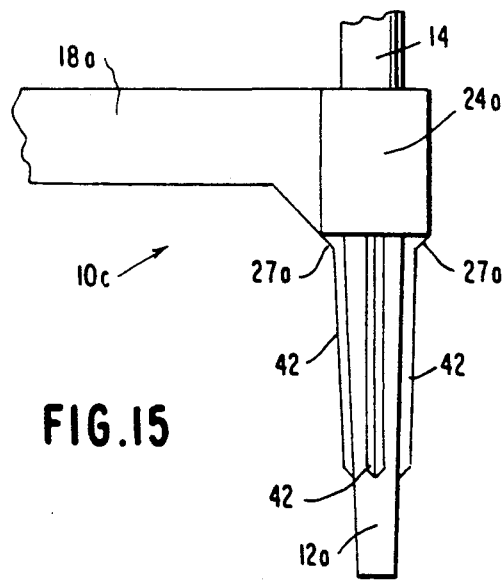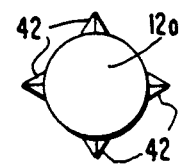

FIG.22A
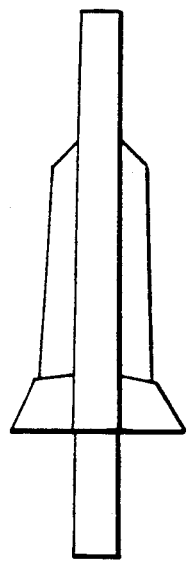
FIG.22B

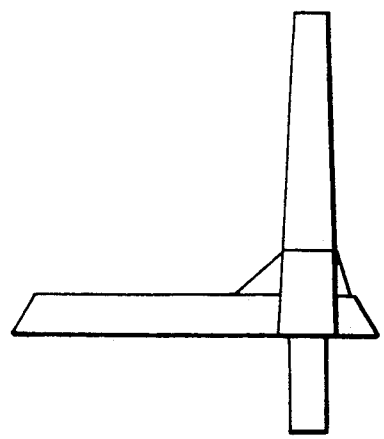
FIG.23
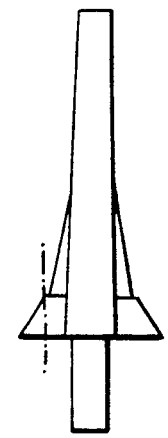
FIG.24

ONE-PIECE CAST RESIN DENTAL DOWEL WITH VISIBLE HORIZONTAL INDEX

This application is a continuation-in-part of my prior pending application No. 07/809,336, filed Dec. 18, 1991 now U.S. Pat. No. 5,222,891.

FIELD OF THE INVENTION

My invention relates generally to the field of dental models and, more particularly, to a novel dowel-pin for a tooth die, and to a method of making a dental model incorporating such a dowel-pin.

The present invention is an improvement of my prior invention described and claimed in my prior U.S. Pat. No. 4,840,565, issued Jun. 20, 1989, and entitled, "Tooth-Die Dowel-Pin and Locking Assembly and Method of Making a Dental Model Incorporating Said Assembly". This patent is expressly incorporated herein by reference for its background information.

In order to fabricate a crown or inlay on a tooth, an impression of a patient's mouth is taken, and a reproduction is made in the dental laboratory. Since the reproduction is a solid positive model of the mouth, it is necessary to isolate reproductions or dies of the individual teeth which have been prepared to receive a restoration. This isolation is accomplished by various types of dowel pins, each of which is secured to a respective die by either a first known process wherein a dowel-pin is inserted into the impression material before the dental model is fabricated, or a second known process wherein the entire solid dental model is first made and, then, holes are drilled above the individual prepared tooth areas or dies to receive individual dowel pins which are inserted and glued into the drilled holes.

In the fabrication of dental models and individual tooth dies, it is extremely important to have both an accurate reproduction of each tooth die and also of the relationship between each individual die and the adjacent model teeth. Since the natural teeth that are positioned in the dental arch are stationary, each individual die on the dental model must be accurately positioned with respect to the entire model so as to correspond to the natural teeth. If there is any movement of the die in the model, then the fabrication of a dental restoration (crown, inlay, etc.) will not be accurate, because, then, the model will not be an accurate reproduction of the natural teeth.

Furthermore, when individual crowns are to be fabricated to restore two or more natural teeth and are to be intentionally joined (soldered) on the model, any movement of the die or dies will cause the final restoration to be inaccurate since the movement of the dies creates an inaccurate reproduction of the natural teeth. Similarly, when crowns are fabricated on dies, and removable appliances are fabricated to be inserted on or into these crowns, any movement of the dies would produce an inaccurate restoration for obvious reasons.

The prior art is replete with various types of dowel pins for incorporation into each individual die. For example, there are (a) single vertical dowel pins with tapers, (b) double vertical pins and (c) single and double vertical pins with corresponding sleeves that are embedded into the stone model. In each case, the intention is to isolate each individual die, and the purpose of the single or double vertical pins is to prevent movement of the die on the master model. Since each die, with its inserted dowel-pin, rests upon the base of the dental model, and since this base has a flat surface, the only security of the die is the vertical dowel that penetrates into the base. As a result, a fulcrum or pivoting effect commonly occurs since there is nothing to prevent the vertically extending conventional dowel-pin from moving. As a result of this fulcrum effect, the die can move in five directions: bucally; lingually; mesially; distally; and also upwardly since there is also nothing available to prevent upward movement of the dowel-pin. Furthermore, often the die bottom that rests upon the flat base surface of the dental model is rough, broken or contains debris that prevents the die from properly seating on the surface of the model base. As a result, and in addition to the fulcrum effect of such a vertical dowel-pin, there is produced an inaccuracy in the relationship of the die to the model and, consequently, an inaccuracy in the fabrication of any restoration which is to be installed on the natural teeth. In addition, since dental models are not standard, and since tooth lengths are not standard, it is often necessary to have an extremely long die. Furthermore, dental models may be of different thicknesses. As a result, it should be clear that, as the length of the die increases, or as the thickness of the dental model increases, the so-called fulcrum effect of the die and dowel-pin also increases. Since there is no standard length of die or model, the conventional dowel-pin or pins do not prevent movement of the die relative to the model.

There are many U.S. patents relating to means for positioning the dowel-pin when making a dental model according to the first process cited above, i.e., a process wherein the dowel-pin is positioned within a negative impression which is then filled with dental material or plaster which surrounds and embeds the dowel-pin, as opposed to the second process (with which my invention is associated) wherein the entire negative impression is filled with dental material or plaster to produce a positive master casting or model into which holes are selectively drilled for receiving subsequently inserted dowel-pins.

U.S. Pat. No. 2,851,728 shows a dental dowel-pin having a single hole therein for receiving an elongated, rod-like repositioning gauge supported in the base stone of a dental model; thus, there is no provision for preventing the above-mentioned fulcrum effect. Furthermore, the single rod-like gauge passes through more than one dowel-pin, a construction which has limited practical value compared to an individual locking device for each dowel pin.

U.S. Pat. Nos. 3,413,725; 3,454,256; and 3,521,354 merely disclose dowel-positioning systems, and also show the use of channel forming members located on the end of a dowel-pin to form a channel in the base stone for facilitating the removal of a selected tooth die from the stone.

U.S. Pat. No. 4,457,709 shows a coiled wire rod for holding a dowel-pin in position in a dental cavity of a tooth impression during the pouring of dental die casting material into the cavity.

U.S. Pat. No. 3,896,548 shows a dental model provided with horizontal wedges which are inserted in mating sockets spanning the parting lines between adjacent tooth dies for maintaining alignment of the tooth dies within the model.

U.S. Pat. Nos. 4,056,585 and 4,139,943 show dowel-pin constructions for use in a dental die.

U.S. Pat. No. 4,997,370 describes a two-piece metal dowel-pin which prevents rotation of a tooth die but having an index which is invisible after the model has been trimmed. This patent is also expressly incorporated herein by reference for its background information.

U.S. Pat. No. 3,470,614 describes a one-piece plastic dowel-pin which requires a "parting plate" and which is useful only in a single-pour process, as opposed to the two-pour process for which my novel dowel-pin is designed. This patent also is expressly incorporated herein by reference for its background information.

U.S. Pat. No. 4,363,625 merely broadly shows a dowel-pin with four ribs, and is of only background interest.

U.S. Pat. No. 4,371,340 merely broadly shows a dowel-pin having an arm, and also is of only background interest.

U.S. Pat. No. 4,721,464 merely shows a dowel-pin having a "parting guide" extending flush with an outer surface of a dental model.

SUMMARY OF THE INVENTION

Therefore, the object of my invention is to provide an improved dowel-pin which is one-piece, which is molded or cast from plastic, which has a horizontal locking index which is visible after the model to which the tooth-die has been inserted is trimmed, and which has integral anti-rotation ribs.

BRIEF DESCRIPTION OF THE DRAWING

FIG. 1 is a perspective view of a first embodiment of my one-piece cast resin dental dowel-pin having an horizontal index in accordance with my invention;

FIG. 2 is a cross-sectional view showing the novel dowel-pin inserted in a tooth-die before the glue has hardened;

FIG. 3 is a cross-sectional view, similar to that of FIG. 2, showing the tooth die after the glue has hardened and after the second half of the model has been poured;

FIG. 4 is a cross-sectional view, similar to that of FIG. 2, showing the novel dowel-pin and its horizontal index, after the model has been trimmed;

FIG. 5 is a front view of the final model showing the triangular shape of the horizontal index and showing the inserted dowel-pin in dashed lines;

FIG. 6 is a front view, similar to that of FIG. 5, but showing only the horizontal triangular index which is actually visible or exposed after trimming of the die;

FIG. 7 is a front view showing the model and the tooth-die in which the novel dowel-pin is inserted, after the tooth-die has been removed from the model;

FIG. 8 is a perspective upside-down view of the model after the tooth-die has been removed, and showing the complementary triangular recess which was formed in the model for receiving the horizontal index of the novel dowel-pin;

FIGS. 9A and 9B are front and side views, respectively, of the novel dowel-pin, and show dimensions of a typical dowel-pin;

FIG. 10A is an enlarged perspective view, in an upside-down position, of the first embodiment of my invention;

FIG. 10B is a cross-sectional view showing the cylindrical configuration of the fastening end of the dowel-pin;

FIG. 10C and 10D are cross-sectional views showing that the free end-portion of the dowel-pin is tapered and has one flat side;

FIG. 11 is a perspective view of a finished dental model containing a plurality of tooth-dies locked in place with my novel dowel-pin having a horizontal index which is visible to an observer;

FIG. 12 is similar to FIG. 11, except that there has been removed from the dental model one of the tooth dies in which my novel dowel-pin has been fixed, and shows the corresponding V-shaped complementary groove or recess in the corresponding vacant location of the model;

FIG. 13 is a perspective view of another embodiment of my novel dowel-pin;

FIGS. 13A, 13B and 13C are cross-sectional views of three different portions of the embodiment of FIG. 13;

FIG. 14 is a perspective view of a third embodiment of the invention, which embodiment is similar to that of FIG. 13 but which has a horizontal index projecting from only one side of the dowel-pin;

FIGS. 14A, 14B and 14C are cross-sectional views of three different portions of the embodiment of FIG. 14;

FIG. 15 is a side view of a fourth embodiment of the invention; and

FIG. 15A is a bottom view of FIG. 15.

FIGS. 16, 17, 18, 19A-D, 20A-D, 21A-D, 22A-D, 23 and 24 illustrate additional preferred embodiments of my invention.

DESCRIPTION OF PREFERRED EMBODIMENTS

Figure 16:
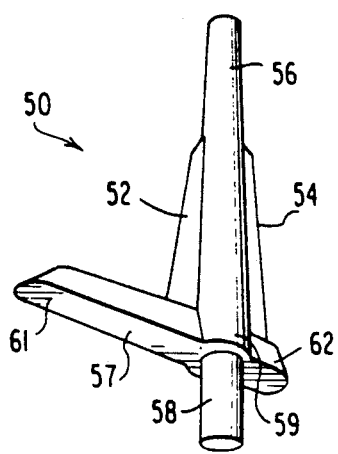

FIG. 1 illustrates a first embodiment of my novel one-piece resin cast dowel-pin which is cast or molded as a rigid single piece from an engineering thermoplastic resin such as a polycarbonate resin. While almost any rigid plastic is suitable, I have found resins belonging to the acetal polymer family, particularly glass-filled, to be preferable. The following are examples of resins which I have purchased to manufacture my dowel pin: Dupont's Delrin 525; Celanese's M-270; and Thermocomp IF-1008 and Thermocomp RF-100-12 manufactured by LNP Engineering Company. The basic integral components of the novel dowel pin comprise a tapered free end-portion 12, a knurled fastening end-portion 14 which is longitudinally aligned with the tapered end-portion 12, and a transverse index 16 which has a long index-segment 18 extending in one direction from the junction of the end-portions 12 and 14, and which has a shorter index-segment 19 extending in the opposite direction from this junction. In use, the end-portions 12 and 14 have a vertical orientation, and the index 16 has a horizontal orientation.

As shown more clearly in FIGS. 10A, 10B, 10C and 10D, the tapered free end-portion 12 has at least one flat surface 20 which prevents rotation of the dowel pin 10 (and of the tooth die 22 fixed thereto) within the dental model 26 as shown, for example, in FIG. 3 and FIG. 4; the tapered free end-portion 12 can have up to four flat surfaces. The knurled fastening-end portion 14 has a cylindrical shape with a circular cross-section as shown more clearly in FIGS. 10A and 10B. My novel dowel-pin is cast or molded so that in this embodiment it has a reinforcing cylindrical collar 24 formed at the junction or intersection of free end-portion 12, fastening end-portion 14, the long index segment 18 and the short index segment 19. For improved strength and rotation prevention, fillets 27 are formed at one or both of the connection points of collar 24 with the index segments 18 and/or 19. These fillets 27 merge with respective ones of the index segments 18 and 19; extend longitudinally along the free end portion 12, and project transversely outwardly in opposite directions. The conventional taper of the free end portion 12 allows the dowel-pin 10 to be removed from the dental model 26.

With reference to FIG. 2, glue is placed on the fastening-end portion 14 for cementation in a bore hole which was formed in the tooth die 22 during the first pour of dental stone-mix, and, at the same time, a small amount of glue is also placed under the index-segments 18 and 19 at their interface with the upper surface of the tooth die 22.

As shown in FIG. 3, after the glue has hardened, the second half of the dental model 26 is poured, using a stone-mix with the usual rubber mold 30; the second pour extends beyond the outer tips 32 and 34 of the long and short index-segments 18 and 19, respectively.

As clearly shown in FIG. 4, when the resulting rough model 26 is "trimmed" at one side 36, for example, the trimmed outer end 38 of the long index-segment 18 is flush with the trimmed side 36 and is visible or exposed to human observation in the trimmed final model. This visible triangular outer end 38 is also shown in the front views of FIGS. 5 and 6. FIGS. 7 and 8 are front and perspective views, respectively, showing the tooth die 22 (with my novel dowel-pin affixed thereto) removed from the final dental model 26 and showing therein the corresponding V-shaped groove or recess 40 which was formed during the second pour of the stone-mix and which receives the horizontal index 16 with its triangular long and short index-segments 18 and 19 for locking the dowel-pin against rotation in the model. FIG. 8 shows the dental model in an upside-down position.

Thus, it is clear that my novel dowel-pin construction has at least two major advantages over prior art constructions: (1) the interlocking of the triangular horizontal index 16 with the correspondingly-shaped recess or groove 40 provides a highly stable construction which prevents rotation of the tooth die within the dental model; and (2) the exposed tip 38 of the horizontal index-segment 18 provides a tooth die "seat" which is visible to a dentist or dental technician, whereas in the prior art there was no standard method of observing the seat of the tooth die.

Because of the selected length of the long horizontal index-segment 18, even after model trimming there will always be the visible index tip 38 to permit a person to ascertain the exact "seat" of the tooth die; in prior art dowel pins with a horizontal index, the index is buried within the final dental model and is not visible, thereby not enabling a human observer visually to ascertain the exact seat of the tooth die.

FIGS. 9A and 9B show preferred dimensions (in millimeters) of this first embodiment of my invention.

FIG. 11 illustrates a dental model 26 showing inserted therein a plurality of tooth dies 22 containing my novel dowel-pin, and also shows the visible horizontal index tips 38.

FIG. 12 is similar to FIG. 11 but shows one of the tooth dies removed from the dental model, thereby exposing the corresponding locking groove or recess 40 containing a bore hole 12a for receiving the removably insertable tapered free end 12 of the dowel-pin 10.

FIGS. 13, 13A, 13B and 13C are similar to FIGS. 10A, 10B, 10C and 10D and show a second embodiment of the invention wherein the collar 24a is square or rectangular (rather than circular).

FIGS. 14, 14A, 14B and 14C show a third embodiment of the invention wherein the dowel-pin 10b has only a longer horizontal index-segment 18a; that is, there is no shorter horizontal index-segment 19 as found in the first and second embodiments of the invention.

FIGS. 15 and 15A show a fourth embodiment which is like the previous embodiments but in which the dowel-pin 10c has a tapered free end-portion 12a having a circular cross-section. Projecting outwardly from the surface of the end-portion 12a are from one to four longitudinally extending ribs or radii 42 which, like the flat surface(s) 20 of the previous embodiments, lock the dowel pin against rotation when inserted in the dental model. The ribs 42 are connected by fillets 27a to index-segment 18a and collar 24a. In a modification of this embodiment, the free end-portion 12a has various combinations of ribs 42 and flat surface(s) 20, such as one flat surface 20 and three ribs 42. The fins 42 are inherently formed during the process of molding the novel dowel pin, and, as illustrated in FIG. 15, one of the ribs 42 merges, via fillet 27a, with the index segment 18a.

Figure 17:
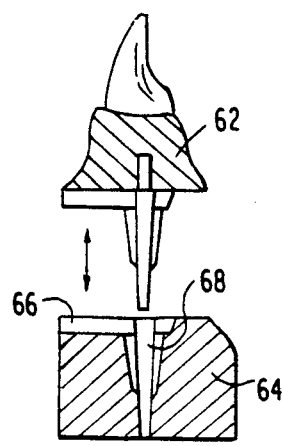
Figure 18:
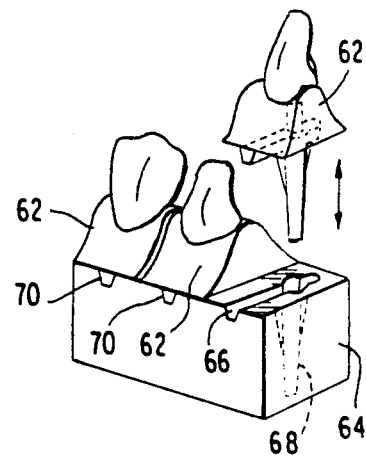
Figure 19A:
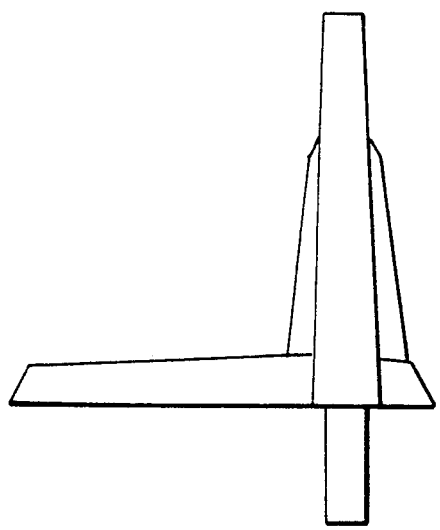
Figure 19B:
Figure 19C:
Figure 19D:
Figure 20A:
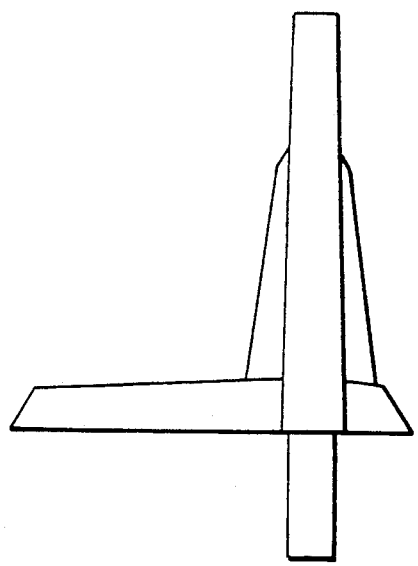
Figure 20B:
Figure 20C:
Figure 20D:
Figure 21A:
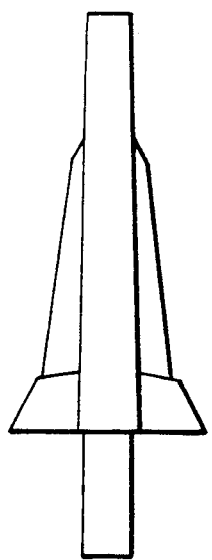
Figure 21B:
Figure 21C:
Figure 21D:
Figure 22C:
Figure 22D:

FIG. 16 is a perspective view of another embodiment of my invention, wherein the one-piece dowel pin 50 is cast or molded with two integral ribs 52 and 54 extending longitudinally upwardly (as viewed in FIG. 16) along the length of the elongated free end-portion 56 which has the form of a cylinder which is tapered upwardly (as viewed in FIG. 16). The integral ribs 52 and 54 are spaced apart by 180° and are molded integrally with the elongated free-end portion 56, the arm portion 57 and the fastening end-portion 58, all of which come together at a junction 59 of the dowel pin. In the embodiment shown in FIG. 16, the arm portion 57 has a first horizontal index segment 61 which projects to the buccal (labial) side, and a shorter second index-segment 62 which projects toward the lingual side. FIGS. 17 and 18 illustrate the manner in which my dowel-pin, after it has been fixed to a tooth die 62 and trimmed, fits into a matching groove 66 and recess 68 in the finally trimmed base model 64. The outer trapezoidally-shaped tip 70 is clearly visible on the buccal side of the finally trimmed based model 64.

As shown in FIGS. 2 and 3, one must always choose a dowel-pin whose horizontal first index-segment 61 is long enough to project beyond the outer periphery 21 of the tooth die formed by the first pour. In this regard, and in order to accommodate dental arches of all sizes, I have found it efficient to manufacture dowel pins having horizontal first index-segments of four different lengths: "large"=13 mm; "medium"=10 mm; "small"=2.5 mm; and "mini"=2.0 mm. However, as the first index-segment becomes shorter, I increase the width and/or length of the longitudinal ribs in order better to prevent rotation of the dowel-pin when it is inserted in the groove 66 and recess 68 of the finally trimmed base model 64. FIGS. 19, 20, 21 and 22 illustrate dowel-pins having first index-segments of these different lengths, together with other relevant dimensions of the dowel-pin for each length. In FIGS. 19–22, the length of each rib is constant at approximately ⅜ the length of the elongated free end portion and stops about 5 mm short of the free tip of the free end-portion 56. The sum of the thickness of the integral arm portion (at the junction) plus the length of a rib is approximately 4/5 the length of the elongated free end portion, and the overall length of the dowel-pin typically is 21.5 mm. The maximum buccal-to-lingual transverse width of my dowel-pin varies from approximately 18.5 mm for the "large" dowel-pin to approximately 7.0 mm for the "mini" dowel-pin. Alternatively, and as shown in FIGS. 23 and 24, (1) for the longer first index-segments, the transverse width of at least one integral rib may be made much wider, while reducing the length of the rib, and (2) for shorter first index-segments, the transverse width is made shorter, while the longitudinal length of the ribs is made greater.

Since it would not be feasible to manufacture a dowel-pin to accommodate all sizes of dental arches, and since it would involve a waste of material to manufacture all dowel-pins with the longest first index-segment ("large"), I have compromised by manufacturing dowel-pins having these four different sizes of horizontal first index-segments, the proper one of which can be selected by a dental technician to fit a particular dental arch. In general, the transverse width and/or the longitudinal length of the ribs for each dowel-pin varies inversely with the length of the horizontal first index-segment in order to provide a maximum anti-rotation capability for the dowel-pin when it is inserted (fixed to the tooth die) in the groove and recess of the base model.

As illustrated, the outer free ends of the first and second horizontal index-segments are tapered, the upper end of each integral rib is inwardly tapered, and the thickness of the integral ribs is tapered, to provide a runoff path when rinsing any debris that may have accumulated between a tooth die and the base model as a tooth die (fixed to a dowel-pin) is being removed from and inserted in the base model. The first and second index-segments also have upper surfaces (facing in the direction of the free end of the elongated free end-portion of the dowel-pin) which taper downwardly as viewed in FIGS. 19–22 in opposite directions transverse to the longitudinal axis of the elongated free end-portion. Furthermore, another taper is formed by the fact that the integral arm-portion, including the first and second index-segments, has a cross-section in the form of an equilateral trapezoid whose short base faces the elongated free end-portion and whose longer base faces the fastening end-portion of the dowel pin. All of these tapered surfaces also provide for easy removal of the dowel-pin from the model after the second pour is made and from the finally trimmed base model after each reinsertion of the dowel-pin (fixed to the tooth die) into the base model.

Even though I have described and illustrated only several embodiments of my invention, it is to be understood that obvious variations of these embodiments are encompassed by my invention the scope of which is limited only by the appended claims.

What is claimed is:

1. A one-piece molded non-metallic plastic dental dowel-pin in combination with a tooth die for use in a finally trimmed dental model that was made by a two-pour process, said combination comprising:
    a tooth die made by a first pour and having an outer periphery and an upper surface and for use with a base model made by a second pour and having a groove therein, said dowel-pin being adapted to be fixed to said tooth die and to be removably inserted in a bore in said base model; said dowel-pin comprising:
    a fastening end-portion extending in a first direction and adapted to be fixed to said tooth die;
    an elongated cylindrical free end-portion which has an outer surface, which has a length extending in a direction opposite to said first direction, and which is adapted to be removably inserted in said base model; and
    an integral elongated locking-and-indexing arm portion having a first index-segment extending from a junction of said fastening and free end-portions in a transverse direction relative to said first and opposite directions; said arm portion matching and being adapted to be received in said groove in said base model when said free end-portion is inserted in said base model; said first index-segment having a length which is sufficiently long to extend along said upper surface and outwardly beyond said outer periphery of said tooth die so that, after the dental model has been finally trimmed, an outer tip of said first index-segment is visible in an outer surface of said base model;
    wherein said arm portion has a second index-segment which extends in a direction opposite to that in which said first index-segment extends, and which, after the dental model has been finally trimmed, is buried inside the dental model and is invisible on the outer surface of the dental model;
    wherein said elongated free end-portion has at least two longitudinally extending integral ribs which project substantially transversely outwardly in opposite directions from said outer surface of said elongated free end-portion, and each of which has a transverse width and a longitudinal length; and
    wherein said length of said first index-segment varies inversely with one of (1) said transverse width and (2) said longitudinal length in order to prevent rotation of said tooth die when inserted in said base model.

2. A one-piece molded non-metallic plastic dental dowel-pin as defined in claim 1, wherein said outer surface of said elongated free end-portion is a tapered cylinder.

3. A one-piece molded non-metallic plastic dental dowel-pin as defined in claim 1, wherein outer surfaces of said first index-segment, said second index-segment, said integral ribs and said elongated free end-portion are tapered to enable easy removal of the dowel-pin from the base model after the second pour and from the finally trimmed model, and to provide a run-off path for accumulated debris rinsed from between said tooth-die and the base model when the tooth die is removed from, and reinserted in, the base model.

4. A one-piece molded non-metallic plastic dental dowel-pin as defined in claim 1, wherein said second index-segment has a length which is shorter than said length of said first index-segment.

5. A one-piece molded non-metallic plastic dental dowel-pin as defined in claim 1, wherein said second index-element has a length which is the same as said length of said first index-segment.

6. A one-piece molded non-metallic plastic dental dowel-pin as defined in claim 1, wherein said longitudinal length of each integral rib extends from said junction toward, and terminates short of, an outer free tip of said elongated free end-portion.

7. A one-piece molded non-metallic plastic dental dowel-pin as defined in claim 6, wherein said longitudinal length of each integral rib is approximately ⅔ the length of said elongated free end-portion.

8. A one-piece molded non-metallic plastic dental dowel-pin as defined in claim 7, wherein said locking-and-indexing arm portion has at said junction a thickness extending in the direction of the length of said elongated free end-portion, and wherein the sum of said thickness plus said longitudinal length of each integral rib is approximately 4/5 the length of said elongated free end-portion.

9. A one-piece molded non-metallic plastic dental dowel-pin as defined in claim 8, wherein said thickness is approximately 2.0 mm, said length of said integral rib is approximately 9.5 mm, and said sum is approximately 11.5 mm, and wherein said dowel-pin has an overall length of approximately 21.5 mm.

10. A one-piece molded non-metallic plastic dental dowel-pin as defined in claim 1, wherein said integral elongated locking-and-indexing arm portion has a transverse cross-section in the shape of an equilateral trapezoid whose short base faces said elongated free end-portion, and whose longer base faces said fastening end-portion.

* * * * *